(12) United States Patent
Turski

(10) Patent No.: US 12,337,001 B2
(45) Date of Patent: Jun. 24, 2025

(54) NEUTRAL ENDOPEPTIDASE (NEP) AND HUMAN SOLUBLE ENDOPEPTIDASE (hSEP) INHIBITORS TO REDUCE DETRIMENTAL EFFECTS OF PERFUSION DEFICIENCY OF PARENCHYMAL ORGANS

(71) Applicant: Christopher Turski, Waunakee, WI (US)

(72) Inventor: Christopher Turski, Waunakee, WI (US)

( * ) Notice: Subject to any disclaimer, the term of this patent is extended or adjusted under 35 U.S.C. 154(b) by 500 days.

(21) Appl. No.: 16/964,984

(22) PCT Filed: Jan. 31, 2019

(86) PCT No.: PCT/PL2019/000013
§ 371 (c)(1),
(2) Date: Jul. 26, 2020

(87) PCT Pub. No.: WO2019/151883
PCT Pub. Date: Aug. 8, 2019

(65) Prior Publication Data
US 2021/0047352 A1    Feb. 18, 2021

(30) Foreign Application Priority Data

Jan. 31, 2018  (PL) .......................... 424453

(51) Int. Cl.
| A61K 31/55 | (2006.01) |
| A61K 31/675 | (2006.01) |
| A61P 25/00 | (2006.01) |
| C07D 225/06 | (2006.01) |
| C07F 3/04 | (2006.01) |
| C07F 9/553 | (2006.01) |

(52) U.S. Cl.
CPC ............ *A61K 31/55* (2013.01); *A61K 31/675* (2013.01); *A61P 25/00* (2018.01); *C07D 225/06* (2013.01); *C07F 3/04* (2013.01); *C07F 9/5535* (2013.01)

(58) Field of Classification Search
CPC ...... A61K 31/55; A61K 31/675; A61K 38/05; C07D 225/06; C07F 3/04; C07F 9/5535; A61P 1/00; A61P 5/00; A61P 25/00; A61P 9/00; A61P 13/02; A61P 13/12; A61P 15/00; A61P 17/00; A61P 27/00
See application file for complete search history.

(56) References Cited

U.S. PATENT DOCUMENTS

| 5,677,297 | A | 10/1997 | Waldeck | |
| 5,783,573 | A | 7/1998 | Rozsa | |
| 5,952,327 | A | * | 9/1999 | Waldeck | ........... A61P 9/04 540/487 |
| 2005/0153936 | A1 | * | 7/2005 | Ikonomidou | ........ A61K 31/675 514/80 |
| 2023/0118503 | A1 | | 4/2023 | Turski | |

FOREIGN PATENT DOCUMENTS

| AU | 701271 B1 | 1/1999 |
| AU | 746907 B2 | 11/2002 |
| CA | 2473447 A1 | 10/2004 |
| EP | 1706121 A1 | 9/2008 |
| EP | 3746106 B1 | 3/2024 |
| PL | 184336 B1 | 10/2002 |
| RU | 2362563 C2 | 7/2009 |
| WO | WO2003068266 A1 | 8/2003 |
| WO | WO2004062692 A1 | 7/2004 |
| WO | WO2005049035 A1 | 6/2005 |
| WO | WO2005067937 A1 | 7/2005 |
| WO | WO2005112939 A1 | 12/2005 |

OTHER PUBLICATIONS

Rots et al. "Effect of bilateral carotid occlusion on cerebral hemodynamics and perivascular innervation: An experimental rat model" Journal of Comparative Neurology, 2019, vol. 527, No. 14, pp. 2263-2272.*
Isabella WY Mak et al. Am. J. Transl. Res., 2014, 6:114-118 (Year: 2014).*
Tsui JC, Baker DM, Biecker E, Shaw S, Dashwood MR. Altered endothelin-1 levels in acute lower limb ischemia and reperfusion. Angiology, 2004, 55(5):533-539 (Year: 2004).*
Yamashita et al., "Increased production of endothelins in the hippocampus of stroke-prone spontaneously hypertensive rats following transient forebrain ischemia: histochemical evidence," Cell. Mol. Neurobiology, 13:15-23 (1993).
Barone et al., "Endothelin levels increase in rat focal and global ischemia," J. Cereb. Blood Flow Metab. 14: 337-342 (1994).
Yokobori et al., "Preconditioning for traumatic brain injury," Transl. Stroke Res. 4: 25-39 (2013).
Heim et al., "Transient occlusion of carotid arteries leads to disturbed spatial learning and memory in the rat," in Krieglstein J, Oberpichler H (Eds), Pharmacology of Cerebral Ischemia, at 53-56 (WVG, Stuttgart 1990).
Fontenay et al., J. Pharmacology., 1:243-254 (1970).
Krzywinski & Altman, "Error bars," Nat. Methods, 10: 921-922. (2013).

(Continued)

*Primary Examiner* — Joseph K Mckane
*Assistant Examiner* — David M Shim
(74) *Attorney, Agent, or Firm* — Joseph A. Mahoney

(57) ABSTRACT

The invention relates to a novel use of benzazepine, benzoxazepine, benzothiazepine-N-acetic acid and phosphono-substituted benzazepinone derivatives having both neutral endopeptidase (NEP) and/or human soluble endopeptidase (hSEP), and endothelin convertase (ECE), inhibitory activity. The compounds of this invention are useful for the preparation of pharmaceutical compositions to reduce harmful effects of symptomless progressive disseminated perfusion deficiency of organs, or parts thereof, that may be suggestive of systemic diseases.

20 Claims, No Drawings

(56) References Cited

OTHER PUBLICATIONS

Kallakuri et al., "Brain cellular localization of endothelin receptors A and B in a rodent model of diffuse traumatic brain injury," Neuroscience, 168:820-830 (2010).
Maier, "Biphasic elevations in cerebrospinal fluid and plasma concentrations of endothelin 1 after traumatic brain injury in human patients," Shock, 27(6):610-614 (2007).
Nortley, "Amyloid B oligomers constrict human capillaries in Alzheimer's disease via signaling to pericytes," Science, 365:250 (2019).
Nortley, "Amyloid B oligomers constrict human capillaries in Alzheimer's disease via signaling to pericytes," Science, 365:250 (2019) (suppl. pp. 1-15).
Rollin et al., "Downregulation of the atrial natriuretic peptide/natriuretic peptide receptor-C system in the early stages of diabetic retinopathy in the rat," Molecular Vision, 11:216-24 (2005).
Salonia et al., "Endothelin-1 is increased in cerebrospinal fluid and associated with unfavorable outcomes in children after severe traumatic brain injury," J. of Neurotrauma, 27:1819-1825 (Oct. 2010).
Lommatzsch et al., "Elevated endothelin-1 levels as risk factor for an impaired ocular blood flow measured by OCT-A in glaucoma," Scientific Reports, 12:11801 (2022).
Koyama, "Endothelin systems in the brain: involvement in pathophysiological responses of damaged nerve tissues," BioMol Concepts 4: 335-347 (2013).
Barton M. et al., Endothelin: 30 Years from discovery to therapy. Hypertension 74: 1232-1265 (2019).
Rosner J., Reddy V., Lui F. In Neuroanatomy, Circle of Willis. StatPearls Publishing (2024).
Ziv I, Fleminger G, Djaldetti R, Achiron A, Melamed E, Sokolovsky M. Increased plasma endothelin-1 in acute ischemic stroke. Stroke. 1992; 23: 1014-1016.
Chatfield et al., Juguloarterial Endothelin-1 Gradients After Severe Traumatic Brain Injury, Neurocrit. Care 14:55-60 (2011).
File history of counterpart European Patent Appl. No. 19747045.3 (EP3746107) as of Apr. 5, 2024 (256 pages).
Seed et al. The dual endothelin converting enzyme/neutral endopeptidase inhibitor SLV-306 (daglutril), inhibits systemic conversion of big endothelin-1 in humans, Life Sciences 91: 743-748 (2012).
Parvanova et al., Effect on blood pressure of combined inhibition of endothelin-converting enzyme and neutral endopeptidase with daglutril in patients with type 2 diabetes who have albuminuria: a randomised, crossover, double-blind, placebo-controlled trial, Lancet vol. 1, Issue 1, p. 19-27, Sep. 2013 (published online Jun. 13, 2013).
Prasana et al., Human Optic Nerve Head Astrocytes as a Target for Endothelin-1, Investigative Ophthalmology & Visual Science Aug. 2002, vol. 43, 2704-2713.
Hajianfar et al., Pulmonary perfusion deficiency detection in lung subsegments of SPECT/CT images using radiomics and machine learning algorithms, J. of Nuclear Med. 65 [supplement 2]: 241915 (2024).
Hueper et al., Quantitative and semiquantitative measures of regional pulmonary microvascular perfusion by magnetic resonance imaging and their relationships to global lung perfusion and lung diffusing capacity: the multiethnic study of atherosclerosis chronic obstructive pulmonary disease study, Invest. Radiol. 48:223-30 (2013).
Elschot et al., Cerebral Microvascular Perfusion Assessed in Elderly Adults by Spin-Echo Dynamic Susceptibility Contrast MRI at 7 Tesla, Tomography 10:181-192 (2024).
Houde et al., Endothelin-1: Biosynthesis, Signaling and Vasoreactivity, Adv. Pharmacol. 77:143-175 (2016).
Yang et al., Classification of myocardial blood flow based on dynamic contrast-enhanced magnetic resonance imaging using hierarchical Bayesian models, J R Stat Soc Series C. 71:1085-1115 (2022).
Broadbent et al., Myocardial blood flow at rest and stress measured with dynamic contrast-enhanced MRI: Comparison of a distributed parameter model with a fermi function model, Magnetic Resonance in Medicine 70(6): 1591-97 (2013).

\* cited by examiner

NEUTRAL ENDOPEPTIDASE (NEP) AND HUMAN SOLUBLE ENDOPEPTIDASE (hSEP) INHIBITORS TO REDUCE DETRIMENTAL EFFECTS OF PERFUSION DEFICIENCY OF PARENCHYMAL ORGANS

FIELD OF THE INVENTION

Described are dual inhibitors of neutral endopeptidase (NEP) and/or human soluble endopeptidase (hSEP), and endothelin converting enzyme-1 (ECE-1), for the preparation of pharmaceutical compositions to reduce harmful effects of symptomless progressive disseminated perfusion deficiency (blood flow deficiency) of organs, or parts thereof, that may be suggestive of systemic diseases.

SCIENTIFIC BACKGROUND OF THE INVENTION

Deficiency of blood flow through organs is one of the major risk factors for systemic diseases in humans. The progressive diffuse perfusion deficiency of organs occurs in most cases symptomless or with minor symptoms for many months or even years, and at the time is not attributed to a specific disease. For this reason, preventive or curative actions are not taken until the first disease specific clinical symptoms appear and the physician diagnoses the systemic disease. Examples illustrating this situation, well known to the public, include e.g. ischemic heart disease, ischemic stroke, or age-related macular degeneration, or chronic neurodegenerative diseases such as e.g. Parkinson's or Alzheimer's diseases. In all of these conditions, long before the occurrence of any disease specific symptoms, there is a period of slowly progressing disseminated reduction of perfusion of various organs. During this phase, the deficiency of perfusion cannot be attributed to any specific disease. Diseases of the brain, spinal cord, or peripheral nerves, diseases of the eyes, and/or optic nerves, diseases of the heart, cardiovascular, or respiratory systems, diseases of the kidneys and urinary tract, and reproductive system, diseases of the digestive system, pancreas, or liver and bile ducts, diseases of the skin, muscles, bones, or joints, and diseases of the endocrine glands, or parts thereof, are the most common systemic diseases in humans whose pathogenesis is related in part to the progressive reduction in the perfusion of specific organs. Currently, therapy is not available to alleviate the diffuse deficiency of blood flow through organs, or therapy limiting the consequences of symptomless progressive disseminated perfusion deficiency of organs, or parts thereof, which may be suggestive of a systemic disease.

Endothelin is a peptide composed of 21 amino acids that is synthesized and released by the endothelium. Endothelin is produced by cleavage of a Trp-Val bond in the precursor peptide big endothelin (Big ET-1). Endothelin converting enzyme-1 (ECE-1), a membrane-bound metalloprotease, catalyses proteolytic activation of Big endothelin-1 to ET-1 and constitutes a regulatory site controlling production of the active peptide. Endothelin is the human body's most potent vasoactive peptide known to date. Endothelin participates in the regulation of blood pressure in parenchymal organs by means of vasoconstrictor activity. Upon release it causes a decrease in blood flow through the organs followed by hypofunction of involved organs.

Endothelin, apart from affecting blood pressure in organs, influences apoptosis in several cell populations acting via $ET_B$ receptors, and in addition induces proliferation of human optic nerve head astrocytes acting via both $ET_A$ and $ET_B$ receptors (G. Prasanna, R. Krishnamoorthy, A. F. Clark, R. J. Wordinger & T. Yorio (2002) Invest. Ophthalmol. Vis. Sci. 43, 2704-2713).

Neutral endopeptidase (NEP), a zink metallopeptidase, degrades atrial natriuretic peptide type C (CNP) and constitutes a regulatory site controlling concentration of the active peptide. In serum-deprived cells, CNP inhibits apoptosis by causing cGMP elevation. Natriuretic peptide receptor NPrB regulates intracellular cGMP concentration by stimulating particulate guanylyl cyclase (pGC), which activates cGMP-dependent protein kinase G pathway.

Since up-regulation of ET-1 receptors and down-regulation of CNP receptors has been reported to occur in cells subjected to oxidative insults, it prompted us to explore the effects of dual NEP and ECE inhibition on the effects of brain perfusion deficiency in rats resembling symptomless progressive disseminated brain perfusion deficiency as known from humans due to carotid stenosis.

INDUSTRIAL BACKGROUND OF THE INVENTION

The invention relates to a novel use of benzazepine, benzoxazepine, benzothiazepine-N-acetic acid and phosphono-substituted benzazepinone derivatives having neutral endopeptidase (NEP) and/or human soluble endopeptidase (hSEP) inhibitory activity. The compounds of this new invention are useful for the preparation of pharmaceutical compositions to reduce harmful effects of symptomless progressive disseminated perfusion deficiency (blood flow deficiency) of the organs, or parts thereof, that may be suggestive of systemic diseases.

The invention relates to the use of compounds disclosed in the patent EP1706121 B1 for the manufacture of teranostic drugs giving a beneficial effect. A beneficial effect is disclosed herein or apparent to a person skilled in the art from the specification and general knowledge in the art. The invention relates to the use of compounds of the invention for the manufacture of teranostic drugs, the effect of which is not attributed to a specific disease, but to a person in whom the disease may occur. This is a procedure where the appropriate type of drug is selected based on the result of an appropriate diagnostic test in a particular person in the context of personalized medicine. During the period of administration of the teranostic drug, the person does not have a diagnosis of a given disease or condition. More specifically, the invention relates to a new use for the restoration of functional balance in parenchymal organs as measured by the diagnostic biomarkers disclosed herein or apparent to a person skilled in the art from specification and general knowledge in the art. In embodiments of the present invention, specific compounds disclosed herein are used for the manufacture of teranostatic drugs.

Patent EP1706121 B1 refers to the use of certain compounds with a combined inhibitory activity on both neutral endopeptidase, and/or human soluble endopeptidase (hSEP), and endothelin converting enzyme (ECE), for the treatment and/or prophylaxis of neurodegenerative diseases such as traumatic brain injury, acute disseminated encephalomyelitis, epilepsy-related brain damage, spinal cord injury, bacterial or viral meningitis and meningoencephalitis, prion diseases, poisonings with neurotoxic compounds, and radiation-induced brain damage, and for prophylaxis of ischemic stroke, with the proviso that said pharmaceutical compositions do not contain an aldosterone receptor antagonist.

WO 2004/082637, filed on Mar. 18, 2004, and published on Sep. 30, 2004, discloses a method for the prophylaxis or treatment of a very large number of pathological conditions, comprising administering an aldosterone receptor antagonist and an endothelin converting enzyme (ECE) inhibitor. Among the pathological conditions listed are systemic diseases. However, no disclosure regarding the benefit of preferred compounds in these indications has been made, and no uses have been disclosed for the manufacture of teranostatic drugs, the effect of which is not attributed to a specific disease.

The aim of the present invention was to identify specific metalloprotease inhibitors that are beneficial and have a teranostatic value when administered to individuals with an altered diagnostic biomarker rather than with a given disease, and do not contain aldosterone receptor antagonists.

Surprisingly, it now has been found that benzazepine, benzoxazepine, benzothiazepine-N-acetic acid and phosphono-substituted benzazepinone derivatives having neutral endopeptidase (NEP) and/or human soluble endopeptidase (hSEP) inhibitory activity have protective activity in a rat model of brain perfusion deficiency, which is not attributed to a specific disease, can be measured using a diagnostic biomarker, and may suggest central nervous system disease, as in humans. Such property makes them useful to reduce harmful effects of symptomless progressive disseminated perfusion deficiency of organs, or parts thereof, and/or for preparation of pharmaceutical compositions to reduce harmful effects of symptomless progressive disseminated perfusion deficiency of organs, or parts thereof, which may be suggestive of systemic diseases selected from the group consisting of such diseases as e.g. (i) diseases of the brain, spinal cord, or peripheral nerves, or parts thereof, and preferably such as e.g. mild cognitive impairment, cognitive dysfunction after chemotherapy, post-surgical cognitive impairment, Alzheimer's disease, vascular dementia, Lewy body dementia, frontotemporal dementia, senile dementia, AIDS dementia complex, progressive supranuclear palsy, corticobasal degeneration, Parkinson's disease, amyotrophic lateral sclerosis, multiple sclerosis, Huntington's disease, cerebellar ataxia, spinocerebellar ataxia, Friedreich's ataxia, optic neuritis and spinal cord inflammation, autoimmune encephalitis, central nervous system vasculitis, brain injury in the course of epilepsy, mitochondrial encephalomyopathy, neuronal ceroidolipofuscinosis, lysosomal storage diseases of the central nervous system, leukodystrophies, urea cycle disorders, hepatic encephalopathy, hepatorenal syndrome, toxic-metabolic encephalopathy, chronic traumatic encephalopathy, porphyria, prion diseases, neurotoxic poisoning, Guillain-Barre syndrome, chronic inflammatory or autoimmune neuropathies, brain, spinal and peripheral nerve injury induced by radiation and/or chemotherapy, multiple system atrophy, and hereditary spastic paraplegia; (ii) diseases of the eyes, and/or optic nerves, or parts thereof, and preferably such as e.g. acquired macular disorders such as e.g. age-related macular degeneration; neuropathies of the optic nerve, preferably such as e.g. anterior or posterior ischemic optic neuropathy; hereditary fundus dystrophies, preferably such as e.g. cone dystrophy, cone-rod dystrophy, rod dystrophy, Stargardt's disease, Bietti's crystalline corneoretinal dystrophy, familial benign fleck retina, Best vitelliform macular dystrophy, adult-onset vitelliform dystrophy, North Carolina macular dystrophy, familial dominant drusen, and concentric annular macular dystrophy; myopia and degenerative myopia; all forms of primary and secondary glaucoma, preferably such as e.g. primary open-angle glaucoma, normal-tension glaucoma, primary angle-closure glaucoma, pseudoexfoliation syndrome and glaucoma, pigment dispersion syndrome and glaucoma, neovascular glaucoma, inflammatory glaucoma, lens-related glaucoma, traumatic glaucoma, primary congenital glaucoma, iatrogenic induced glaucoma, and malignant glaucoma; (iii) diseases of the heart, cardiovascular, or respiratory systems, or parts thereof, and preferably such as e.g. ischemic heart disease; cardiomyopathies, preferably such as e.g. congestive cardiomyopathy, hypertrophic cardiomyopathy, obstructive cardiomyopathy, right ventricular arrhythmogenic cardiomyopathy, and ischemic, valvular, hypertensive, inflammatory, metabolic, and toxic cardiomyopathy, and cardiomyopathy in the course of systemic diseases, or pregnancy; chronic heart failure; and heart transplant rejection; chronic obstructive pulmonary disease, emphysema, bronchiectasis, bronchiolitis obliterans, bronchopulmonary dysplasia, cystic fibrosis, alpha-1-antitrypsin deficiency, hypersensitivity pneumonitis, idiopathic pulmonary fibrosis, pulmonary fibrosis, lymphangioleiomyosis, sarcoidosis, pneumoconiosis, and preferably such as e.g. silicosis, asbestosis, and anthracosis, or pulmonary transplant rejection; (iv) diseases of the kidneys and urinary tract, and reproductive system, or parts thereof, and preferably such as e.g. polycystic kidney disease, chronic glomerulonephritis, amyloidosis, systemic vasculitides affecting the kidneys, antiphospholipid syndrome; nephropathies, and preferably such as e.g. hypertensive, ischemic, diabetic, autoimmune, obstructive, drug-induced, toxic, or lupus nephropathy; nephrotic syndrome, diffuse renal glomerulosclerosis, hemolytic-uremic syndrome, preeclampsia, renal artery stenosis, renal sarcoidosis, renal transplant rejection, polycystic ovary syndrome, chronic ovarian ischemia, chronic uterine ischemia, endometriosis, chronic testicular ischemia, chronic penile ischemia, chronic prostate ischemia, Peyronie's disease, impotence, and male and female infertility; (v) diseases of the digestive system, pancreas, or liver and bile ducts, or parts thereof, and preferably such as e.g. ischemic esophagitis, ischemic gastritis, ischemic duodenitis, chronic mesenteric ischemia, irritable bowel syndrome, inflammatory bowel disease, Crohn's disease, ischemic or ulcerative colitis, necrotizing enterocolitis, pseudomembranous enterocolitis, radiation-induced enteritis, gastritis and colitis, celiac disease, and chronic gastritis; hepatitis, and preferably such as e.g. ischemic, alcoholic and viral hepatitis, and hepatitis in the course of AIDS, metabolic, autoimmune, and radiation-induced hepatitis; cirrhosis, ischemic cholecystitis, ischemic cholangitis, primary sclerosing cholangitis, sclerosing cholangiopathy associated with IgG4, recurrent purulent cholangitis, portal biliopathy, eosinophilic and mastocytic cholangitis, ischemic cholangiopathy, infectious cholangiopathy in the course of AIDS, liver transplant rejection, chronic ischemic pancreatitis, and pancreatic insufficiency; (vi) diseases of the skin, muscles, bones, or joints, or parts thereof, and preferably such as e.g. pemphigus vulgaris, bullous pemphigoid, eczema, acne, psoriasis, ischemic onycholysis, ischemic dermatopathy, acantholysis, dermatosis, cutaneous lupus erythematosus, scabies, vitiligo, hair loss, alopecia areata; muscular dystrophies, and preferably such as e.g. Duchenne muscular dystrophy, Becker muscular dystrophy, rim-girdle, facioscapulohumeral, Fukuyama congenital, and myotonic muscular dystrophy; polymyositis, dermatomyositis, fibromyalgia, polymyalgia rheumatica, ankylosing spondylitis, mixed connective tissue disease, systemic lupus erythematosus, rheumatoid arthritis, osteochondrosis, osteoporosis, and osteonecrosis; (vii) diseases of the endocrine glands, or parts thereof, and preferably such as e.g. chronic adrenocortical insufficiency, thymus insufficiency in elderly, pineal gland insufficiency, thyroid goiters, panhypopituitarism, postpartum pituitary gland necrosis (Sheehan's syndrome), diabetes insipidus, premature ovarian failure, premature testicular failure, erectile dysfunction, female sexual arousal disorder, female orgasmic disorder (anorgasmia), and female hypoactive sexual desire disorder.

The compounds of the invention are known from the European patents EP 0 733 642, EP 0 916 679 and EP 1 468 010, containing detailed syntheses, and can be described by the general formula (1):

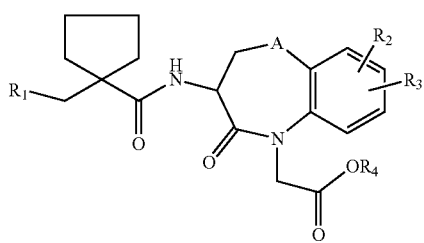

(1)

wherein:
R1 stands for a group with formula (2) or (3):

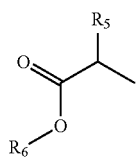

(2)

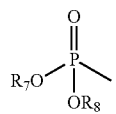

(3)

A represents CH2, O or S,
R2 and R3 independently represent hydrogen or halogen,
R4 and R6 independently represent hydrogen or a biolabile carboxylic ester forming group;
R5 is selected from the group consisting of (C1-C6)-alkoxy-(C1-C6)-alkyl which may be substituted by a (C1-C6)-alkoxy, phenyl-(C1-C6)-alkyl and phenyloxy-(C1-C6)-alkyl wherein the phenyl group may be substituted with (C1-C6)-alkyl, (C1-C6)-alkoxy or halogen, and naphtyl-(C1-C6)-alkyl,
R7 and R8 independently represent hydrogen or a group forming a biolabile phosphonic acid ester.

To the invention belong all compounds having formula (1), racemates, mixtures of diastereomers and the individual stereoisomers, and also include pharmaceutically acceptable salts thereof. Thus compounds in which the substituents on potentially asymmetrical carbon atoms are in either the R-configuration or the S-configuration belong to the invention.

Pharmaceutically acceptable salts may be obtained using standard procedures well known in the art, for example by mixing a compound of the present invention with a suitable metal cation or an organic base, for instance an amine.

This objective can be achieved by preparing the metal salt of the compounds with the general formula (1) as mentioned above wherein the metal ion is a lithium ion or a bivalent metal ion. Preferred bivalent metal salts are calcium, magnesium and zinc salts. Most preferred is the calcium salt.

The invention relates to the use of a compound of general formula (1), as defined above, to reduce harmful effects of symptomless progressive disseminated perfusion deficiency of organs, or parts thereof, and/or for preparation of pharmaceutical compositions to reduce harmful effects of symptomless progressive disseminated perfusion deficiency of organs, or parts thereof, which may be suggestive of systemic diseases selected from the group consisting of such diseases as e.g. (i) diseases of the brain, spinal cord, or peripheral nerves, or parts thereof, and preferably such as e.g. mild cognitive impairment, cognitive dysfunction after chemotherapy, postsurgical cognitive impairment, Alzheimer's disease, vascular dementia, Lewy body dementia, frontotemporal dementia, senile dementia, AIDS dementia complex, progressive supranuclear palsy, corticobasal degeneration, Parkinson's disease, amyotrophic lateral sclerosis, multiple sclerosis, Huntington's disease, cerebellar ataxia, spinocerebellar ataxia, Friedreich's ataxia, optic neuritis and spinal cord inflammation, autoimmune encephalitis, central nervous system vasculitis, brain injury in the course of epilepsy, mitochondrial encephalomyopathy, neuronal ceroidolipofuscinosis, lysosomal storage diseases of the central nervous system, leukodystrophies, urea cycle disorders, hepatic encephalopathy, hepatorenal syndrome, toxic-metabolic encephalopathy, chronic traumatic encephalopathy, porphyria, prion diseases, neurotoxic poisoning, Guillain-Barre syndrome, chronic inflammatory or autoimmune neuropathies, brain, spinal and peripheral nerve injury induced by radiation and/or chemotherapy, multiple system atrophy, and hereditary spastic paraplegia; (ii) diseases of the eyes, and/or optic nerves, or parts thereof, and preferably such as e.g. acquired macular disorders such as e.g. age-related macular degeneration; neuropathies of the optic nerve, preferably such as e.g. anterior or posterior ischemic optic neuropathy; hereditary fundus dystrophies, preferably such as e.g. cone dystrophy, cone-rod dystrophy, rod dystrophy, Stargardt's disease, Bietti's crystalline corneoretinal dystrophy, familial benign fleck retina, Best vitelliform macular dystrophy, adult-onset vitelliform dystrophy, North Carolina macular dystrophy, familial dominant drusen, and concentric annular macular dystrophy; myopia and degenerative myopia; all forms of primary and secondary glaucoma, preferably such as e.g. primary open-angle glaucoma, normal-tension glaucoma, primary angle-closure glaucoma, pseudoexfoliation syndrome and glaucoma, pigment dispersion syndrome and glaucoma, neovascular glaucoma, inflammatory glaucoma, lens-related glaucoma, traumatic glaucoma, primary congenital glaucoma, iatrogenic induced glaucoma, and malignant glaucoma; (iii) diseases of the heart, cardiovascular, or respiratory systems, or parts thereof, and preferably such as e.g. ischemic heart disease; cardiomyopathies, preferably such as e.g. congestive cardiomyopathy, hypertrophic cardiomyopathy, obstructive cardiomyopathy, right ventricular arrhythmogenic cardiomyopathy, and ischemic, valvular, hypertensive, inflammatory, metabolic, and toxic cardiomyopathy, and cardiomyopathy in the course of systemic diseases, or pregnancy; chronic heart failure; and heart transplant rejection; chronic obstructive pulmonary disease, emphysema, bronchiectasis, bronchiolitis obliterans, bronchopulmonary dysplasia, cystic fibrosis, alpha-1-antitrypsin deficiency, hypersensitivity pneumonitis, idiopathic pulmonary fibrosis, pulmonary fibrosis, lymphangioleiomyosis, sarcoidosis, pneumoconiosis, and preferably such as e.g. silicosis, asbestosis, and anthracosis, or pulmonary transplant rejection; (iv) diseases of the kidneys and urinary tract, and reproductive system, or parts thereof, and preferably such as e.g. polycystic kidney disease, chronic glomerulonephritis, amyloidosis, systemic vasculitides affecting the kidneys, antiphospholipid syndrome; nephropathies, and preferably such as e.g. hypertensive, ischemic, diabetic, autoimmune, obstructive, drug-induced, toxic, or lupus nephropathy; nephrotic syndrome, diffuse renal glomerulosclerosis, hemolytic-uremic syndrome, preeclampsia, renal artery stenosis, renal sarcoidosis, renal transplant rejection, polycystic ovary syndrome, chronic ovarian ischemia, chronic uterine ischemia, endometriosis, chronic testicular ischemia, chronic penile ischemia, chronic prostate ischemia, Peyronie's disease, impotence, and male and female infertility; (v) diseases of the digestive system, pancreas, or liver and bile ducts, or parts thereof, and preferably such as e.g. ischemic esophagitis, ischemic gastritis, ischemic duodenitis, chronic mesenteric ischemia, irritable bowel syndrome, inflammatory bowel disease, Crohn's disease, ischemic or ulcerative colitis, necrotizing enterocolitis, pseudomembranous enterocolitis, radiation-induced enteritis, gastritis and colitis, celiac disease, and chronic gastritis; hepatitis, and preferably such as e.g. ischemic, alcoholic and viral hepatitis, and hepatitis in the course of AIDS, metabolic, autoimmune, and radiation-induced hepatitis; cirrhosis, ischemic cholecystitis, ischemic cholangitis, primary sclerosing cholangitis, sclerosing cholangiopathy associated with IgG4, recurrent purulent cholangitis, portal biliopathy, eosinophilic and mastocytic cholangitis, ischemic cholangiopathy, infectious cholangiopathy in the course of AIDS, liver transplant rejection, chronic ischemic pancreatitis, and pancreatic insufficiency; (vi) diseases of the skin, muscles, bones, or joints, or parts thereof, and preferably such as e.g. pemphigus vulgaris, bullous pemphigoid, eczema, acne, psoriasis, ischemic onycholysis, ischemic dermatopathy, acantholysis, dermatosis, cutaneous lupus erythematosus, scabies, vitiligo, hair loss, alopecia areata; muscular dystrophies, and preferably such as e.g. Duchenne muscular dystrophy, Becker muscular dystrophy, rim-girdle, facioscapulohumeral, Fukuyama congenital, and myotonic muscular dystrophy; polymyositis, dermatomyositis, fibromyalgia, polymyalgia rheumatica, ankylosing spondylitis, mixed connective tissue disease, systemic lupus erythematosus, rheumatoid arthritis, osteochondrosis, osteoporosis, and osteonecrosis; (vii) diseases of the endocrine glands, or parts thereof, and preferably such as e.g. chronic adrenocortical insufficiency, thymus insufficiency in elderly, pineal gland insufficiency, thyroid goiters, panhypopituitarism, postpartum pituitary gland necrosis (Sheehan's syndrome), diabetes insipidus, premature ovarian failure, premature testicular failure, erectile dysfunction, female sexual arousal disorder, female orgasmic disorder (anorgasmia), and female hypoactive sexual desire disorder, with the proviso that said pharmaceutical compositions do not contain an aldosterone receptor antagonist.

Further embodiments of the invention are defined in the dependent claims.

The invention particularly relates to the use of compounds having general formula (4):

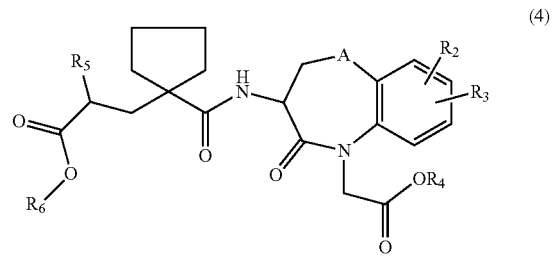

(4)

wherein the symbols have the meanings as given above.

More particular, the invention relates to the use of compounds having general formula (5):

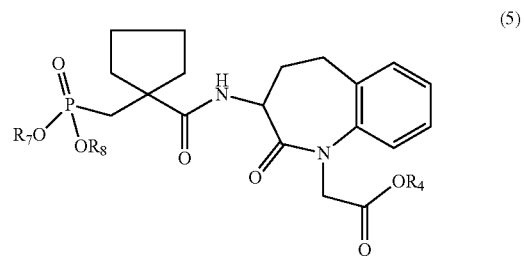

(5)

wherein the symbols have the meanings as given above.

The most preferred active substances used according to the present invention are:

(2R)-2-{[1-({[(3S)-1-(carboxymethyl)-2-oxo-2,3,4,5-tetrahydro-1H-1-benzazepin-3-yl]amino}carbonyl)cyclopentyl]methyl}-4-phenylbutanoic acid (6):

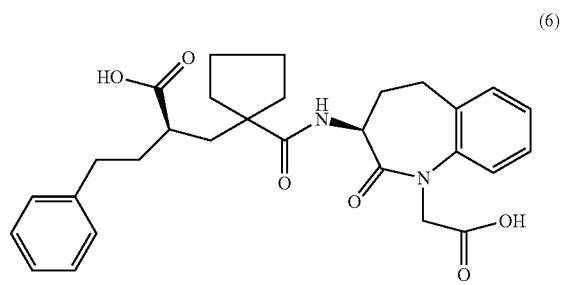 [SMILES: O=C(O)CN1C(=O)[C@@H](NC(=O)C2(C[C@@H](CCc3ccccc3)C(=O)O)CCCC2)CCc2ccccc21]

(6)

(2R)-2-{[1-({[(3S)-1-(carboxymethyl)-2-oxo-2,3,4,5-tetrahydro-1H-1-benzazepin-3-yl]amino}carbonyl)cyclopentyl]methyl}-4-(1-naphthyl)butanoic acid (7):

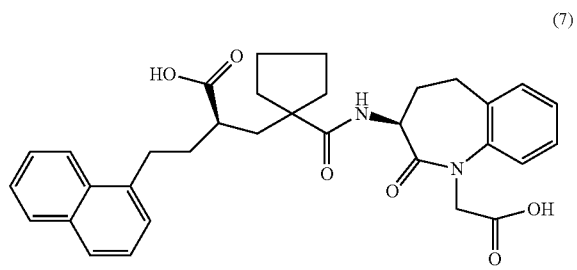 [SMILES: O=C(O)CN1C(=O)[C@@H](NC(=O)C2(C[C@@H](CCc3cccc4ccccc34)C(=O)O)CCCC2)CCc2ccccc21]

(7)

tert-butyl-((3S)-3-{[(1-{[(benzyloxy)(ethoxy)phosphoryl]methyl}cyclopentyl) carbonyl]amino}-2-oxo-2,3,4,5-tetrahydro-1H-1-benzazepin-1-yl)acetate (8):

(8)

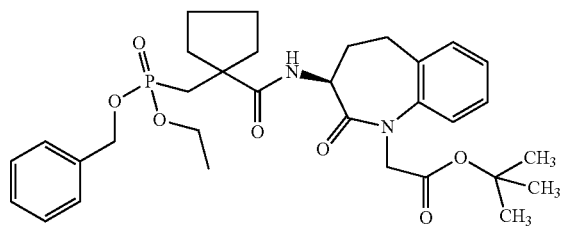

Pharmaceutical Compositions

The compounds of the invention can be brought into forms suitable for administration by means of usual processes using auxillary substances such as liquids or carrier materials. The pharmaceutical compositions of the invention may be administered either systemically and/or topically, and in particular e.g. they may be administered enterally, orally, parenterally (intramuscularly or intravenously), subcutaneously or rectally, or vaginally, or locally (topically) as well as externally, and to the eye, periocularly in such manner as subconjunctival, subtenon, retrobulbar or peribulbar, and intraocularly into the eye. They can be administered in the form of solutions, suspensions, ointments (creams, gels, gel-forming solutions, sprays, ocular inserts/deposits, contact lenses), ocular implants but also tablets, capsules, softgels, powders, suppositories, nano-formulations or via iontophoresis, or by means of pharmaceutical compositions based on nanoparticle carrier systems. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut or sesame oil, polyethylene glycol and solvents such as e.g. sterile water and mono- or polyhydric alcohols such as glycerol.

Compounds of the present invention are generally administered as pharmaceutical compositions. Types of pharmaceutical compositions that may be used include but are not limited to solutions, suspensions, ointments (creams, gels or sprays), but also tablets, chewable tablets, capsules, softgels, parenteral solutions, suppositories, and other types disclosed herein or apparent to a person skilled in the art from the specification and general knowledge in the art. The pharmaceutical compositions of the invention do not contain an aldosterone receptor antagonist.

In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceutical products, which notice reflects approval by the agency of manufacture, use, or sale for human or veterinary administration.

Very specific formulations suitable for the compounds of the invention have been described in the patent applications WO 03/068266 and WO 04/062692.

The specific compounds described above are intended to further illustrate the invention in more detail, and therefore are not deemed to restrict the scope of the invention in any way.

Symptomless Progressive Disseminated Perfusion Deficiency of Organs Suggestive of Systemic Diseases Symptomless progressive disseminated deficiency of blood flow through organs, or parts thereof, is an important factor that may be suggestive of systemic diseases selected from the group consisting of such diseases as e.g. (i) diseases of the brain, spinal cord, or peripheral nerves, or parts thereof, and preferably such as e.g. mild cognitive impairment, cognitive dysfunction after chemotherapy, postsurgical cognitive impairment, Alzheimer's disease, vascular dementia, Lewy body dementia, frontotemporal dementia, senile dementia, AIDS dementia complex, progressive supranuclear palsy, corticobasal degeneration, Parkinson's disease, amyotrophic lateral sclerosis, multiple sclerosis, Huntington's disease, cerebellar ataxia, spinocerebellar ataxia, Friedreich's ataxia, optic neuritis and spinal cord inflammation, autoimmune encephalitis, central nervous system vasculitis, brain injury in the course of epilepsy, mitochondrial encephalomyopathy, neuronal ceroidolipofuscinosis, lysosomal storage diseases of the central nervous system, leukodystrophies, urea cycle disorders, hepatic encephalopathy, hepatorenal syndrome, toxic-metabolic encephalopathy, chronic traumatic encephalopathy, porphyria, prion diseases, neurotoxic poisoning, Guillain-Barre syndrome, chronic inflammatory or autoimmune neuropathies, brain, spinal and peripheral nerve injury induced by radiation and/or chemotherapy, multiple system atrophy, and hereditary spastic paraplegia (W. R. Brown & C. R. Thore (2011) Neuropathol. Appl. Neurobiol. 37, 56-74); (ii) diseases of the eyes, and/or optic nerves, or parts thereof, and preferably such as e.g. acquired macular disorders such as e.g. age-related macular degeneration; neuropathies of the optic nerve, preferably such as e.g. anterior or posterior ischemic optic neuropathy; hereditary fundus dystrophies, preferably such as e.g. cone dystrophy, cone-rod dystrophy, rod dystrophy, Stargardt's disease, Bietti's crystalline corneoretinal dystrophy, familial benign fleck retina, Best vitelliform macular dystrophy, adult-onset vitelliform dystrophy, North Carolina macular dystrophy, familial dominant drusen, and concentric annular macular dystrophy; myopia and degenerative myopia; all forms of primary and secondary glaucoma, preferably such as e.g. primary open-angle glaucoma, normal-tension glaucoma, primary angle-closure glaucoma, pseudoexfoliation syndrome and glaucoma, pigment dispersion syndrome and glaucoma, neovascular glaucoma, inflammatory glaucoma, lens-related glaucoma, traumatic glaucoma, primary congenital glaucoma, iatrogenic induced glaucoma, and malignant glaucoma (Y. Zhang, J. M. Harrison, O. San Emeterio Nateras, S. Chalfin, & T. Q. Duong (2013) Doc. Ophthalmol. 126, 187-197); (iii) diseases of the heart, cardiovascular, or respiratory systems, or parts thereof, and preferably such as e.g. ischemic heart disease; cardiomyopathies, preferably such as e.g. congestive cardiomyopathy, hypertrophic cardiomyopathy, obstructive cardiomyopathy, right ventricular arrhythmogenic cardiomyopathy, and ischemic, valvular, hypertensive, inflammatory, metabolic, and toxic cardiomyopathy, and cardiomyopathy in the course of systemic diseases, or pregnancy; chronic heart failure; and heart transplant rejection; chronic obstructive pulmonary disease, emphysema, bronchiectasis, bronchiolitis obliterans, bronchopulmonary dysplasia, cystic fibrosis, alpha-1-antitrypsin deficiency, hypersensitivity pneumonitis, idiopathic pulmonary fibrosis, pulmonary fibrosis, lymphangioleiomyosis, sarcoidosis, pneumoconiosis, and preferably such as e.g. silicosis, asbestosis, and anthracosis, or pulmonary transplant rejection (P. Abete, D. Della-Morte, G. Gargiulo, C. Basile, A. Langellotto, G. Galizia, G. Testa, V. Canonico, D. Bonaduce & F. Cacciatore (2014) Ageing Res. Rev. 18, 41-52); (iv) diseases of the kidneys and urinary tract, and reproductive system, or parts thereof, and preferably such as e.g. polycystic kidney disease, chronic glomerulonephritis, amyloidosis, systemic vasculitides affecting the kidneys, antiphospholipid syndrome; nephropathies, and preferably such as e.g. hypertensive, ischemic, diabetic, autoimmune, obstructive, drug-induced, toxic, or lupus nephropathy; nephrotic syndrome, diffuse renal glomerulosclerosis, hemolytic-uremic syndrome, preeclampsia, renal artery stenosis, renal sarcoidosis, renal transplant rejection, polycystic ovary syndrome, chronic ovarian ischemia, chronic uterine ischemia, endometriosis, chronic testicular ischemia, chronic penile ischemia, chronic prostate ischemia, Peyronie's disease, impotence, and male and female infertility (A. Saad, S. M. Herrmann & S. C. Textor (2015) Physiology (Bethesda) 30, 175-182); (v) diseases of the digestive system, pancreas, or liver and bile ducts, or parts thereof, and preferably such as e.g. ischemic esophagitis, ischemic gastritis, ischemic duodenitis, chronic mesenteric ischemia, irritable bowel syndrome, inflammatory bowel disease, Crohn's disease, ischemic or ulcerative colitis, necrotizing enterocolitis, pseudomembranous enterocolitis, radiation-induced enteritis, gastritis and colitis, celiac disease, and chronic gastritis; hepatitis, and preferably such as e.g. ischemic, alcoholic and viral hepatitis, and hepatitis in the course of AIDS, metabolic, autoimmune, and radiation-induced hepatitis; cirrhosis, ischemic cholecystitis, ischemic cholangitis, primary sclerosing cholangitis, sclerosing cholangiopathy associated with IgG4, recurrent purulent cholangitis, portal biliopathy, eosinophilic and mastocytic cholangitis, ischemic cholangiopathy, infectious cholangiopathy in the course of AIDS, liver transplant rejection, chronic ischemic pancreatitis, and pancreatic insufficiency (M. Bjôrck & A. Wanhainen (2010) Semin. Vasc. Surg. 23, 54-64); (vi) diseases of the skin, muscles, bones, or joints, or parts thereof, and preferably such as e.g. pemphigus vulgaris, bullous pemphigoid, eczema, acne, psoriasis, ischemic onycholysis, ischemic dermatopathy, acantholysis, dermatosis, cutaneous lupus erythematosus, scabies, vitiligo, hair loss, alopecia areata; muscular dystrophies, and preferably such as e.g. Duchenne muscular dystrophy, Becker muscular dystrophy, rim-girdle, facioscapulohumeral, Fukuyama congenital, and myotonic muscular dystrophy; polymyositis, dermatomyositis, fibromyalgia, polymyalgia rheumatica, ankylosing spondylitis, mixed connective tissue disease, systemic lupus erythematosus, rheumatoid arthritis, osteochondrosis, osteoporosis, and osteonecrosis (M. C. Dalakas (2010) Curr. Opin. Pharmacol. 10, 346-352); (vii) diseases of the endocrine glands, or parts thereof, and preferably such as e.g. chronic adrenocortical insufficiency, thymus insufficiency in elderly, pineal gland insufficiency, thyroid goiters, panhypopituitarism, postpartum pituitary gland necrosis (Sheehan's syndrome), diabetes insipidus, premature ovarian failure, premature testicular failure, erectile dysfunction, female sexual arousal disorder, female orgasmic disorder (anorgasmia), and female hypoactive sexual desire disorder (H. J. Schneider, P. G. Samann, M. Schneider, C. G. Croce, G. Corneli, C. Sievers, F. Ghigo, G. K. Stalla, & G. Aimaretti (2007) J. Endocrinol. Invest. 30, RC9-RC12). To model symptomless progressive disseminated deficiency of blood flow through the brain in the non-human experiment, rats were subjected to bilateral transient occlusion of the carotid arteries while maintaining patency of the vertebral arteries, and maintaining normal blood pressure. To determine whether the examples representative for the compounds of the present invention protected the brain from the harmful effects of perfusion deficiency, we used a model of a transient bilateral occlusion of the common carotid artery in normotensive rats (BCCA) (C. Heim, M. Sieklucka, F. Block, R. Schmidt-Kastner, R. Jaspers & K.-H. Sontag (1990) *Pharmacology of cerebral ischemia*, J. Krieglstein & H. Oberpichler, W V G, Stuttgart, pp. 53-61), which is the experimental equivalent of a deficiency in brain perfusion caused by carotid stenosis in humans.

EXAMPLES

Methods: Wistar rats, 200-250 g, were anesthetized with chloral hydrate, 400 mg/kg, and osmotic minipumps, primed prior to implantation, were filled with either vehicle or example (6), representative for the compounds of the invention, in the dose of 60 mg/kg/d, and were implanted subcutaneously. Subsequently, rats (n=8) were subjected to transient bilateral occlusion of the common carotid artery (BCCA) for 30 min with surgical thread under sodium pentobarbital anaesthesia in the dose of 60 mg/kg i.p. on day 2. The interruption of the blood flow in carotid arteries was visually controlled, after 30 min the threads were removed, and the surgical field closed. In sham-operated control rats (n=8), blood flow in the carotid arteries was not interrupted, but sutures were placed and subsequently removed. The exploratory performance of rats was evaluated in the open field test (M. Fontenay, J. Le Cornec, M. Zaczyńska, M. C. Debarle, P. Simon & J. R. Boissier (1970) J. Pharmacol. 1, 243-254). The animals were placed in an open field for a period of 5 min and ambulation, rearing, grooming, episodes of interests in blocks, and number of defecations were counted. The tests were carried out 5 days after BCCA (n=8). Statistical evaluation was performed by means of the Mann-Whitney U test.

Results: Transient bilateral occlusion of the common carotid artery (BCCA) for 30 min significantly disrupted exploratory behavior of rats as measured in the open field test by the number of rearings (45.12%) and the episodes of interest in blocks (48.64%), while ambulations (105.05) %), grooming (114.53%), and defecations (76.19%) did not significantly change (Table 1). Compound (6) induced statistically significant improvement of exploratory performance in rats subjected to BCCA, as evidenced by the normalization of rearings (104.62%) and the episodes of interest in blocks (103.80%) without affecting ambulations (94.81%), as compared to the sham-operated controls (Table 1).

Conclusions: The compound of formula (6) induced a significant improvement of exploratory performance reduced by transient deficiency of brain perfusion caused by bilateral occlusion of the common carotid artery (BCCA), as evidenced by the normalization of rearing and episodes of interests in blocks without changing the ambulations, grooming, and defecations in the open field test (Table 1).

TABLE 1

Effect on exploratory performance of rats in the open field.

| | Ambulation (n) | Rearing (n) | Blocks (n) | Grooming (n) | Defecation (n) |
|---|---|---|---|---|---|
| Control + (6) | 28.91 ± 5.13 | 11.48 ± 3.51 | 7.36 ± 2.85 | 5.30 ± 1.57 | 1.26 ± 0.45 |
| % | 100 | 100 | 100 | 100 | 100 |
| BCCA | 30.37 ± 3.22 | 5.18 ± 2.05*[a] | 3.58 ± 1.57*[a] | 6.07 ± 1.38 | 0.96 ± 0.31 |
| % | 105.05 | 45.12 | 48.64 | 114.53 | 76.19 |
| BCCA + (6) | 2741 ± 4.25 | 12.01 ± 3.86 | 7.64 ± 2.54 | 5.98 ± 1.06 | 1.04 ± 0.45 |
| % | 94.81 | 104.62 | 103.80 | 112.83 | 82.54 |

*P < 0.05 BCCA vs Control + (6);
[a]P < 0.05 BCCA vs BCCA + (6);
Mann-Whitney U-test; x̄ ± SEM, BCCA, bilateral occlusion of common carotid arteries.

The invention claimed is:

1. A method of treating perfusion deficiency of an organ or part thereof in a human subject as measured by an elevated concentration of a biomarker in one or more bodily fluids wherein the organ is the brain or part thereof, comprising administering a therapeutically effective amount of a compound of the general formula (4):

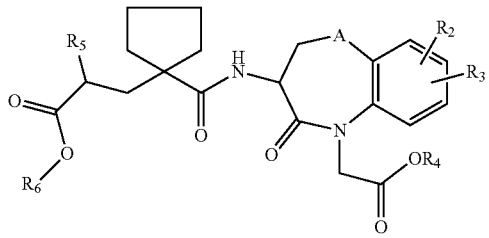

(4)

wherein A is CH$_2$,
wherein R2 and R3 independently represent hydrogen;
R4 and R6 independently represent hydrogen or a group that forms a biolabile carboxylic ester; and R5 is selected from the group consisting of -alkyl-(C1-C6)-phenyl, and -alkyl-(C1-C6)-naphthyl,
or a pharmaceutically acceptable salt or stereoisomer thereof; wherein the biomarker is selected from the group consisting of Endothelin-1 biomarker, pre-Endothelin-1, Pro-Endothelin (Big Endothelin-1), endothelin-1 converting enzyme (ECE-1), neutral endopeptidase (NEP), human soluble endopeptidase (hSEP), and combinations thereof.

2. The method as recited in claim 1, wherein the pharmaceutically acceptable salt is selected from the group consisting of lithium salt, calcium salt, magnesium salt, and zinc salt.

3. The method as recited in claim 2, wherein the pharmaceutically acceptable salt is calcium salt.

4. The method as recited in claim 1, wherein the compound is administered parenterally to the subject at a dose of about 60 mg/kg per day.

5. The method as recited in claim 1, wherein the compound is administered subcutaneously.

6. The method as recited in claim 1, wherein the compound is administered as an implant.

7. The method as recited in claim 1, wherein the bodily fluid is selected from the group consisting of blood, blood plasma, saliva, tears, sweat, urine, cerebrospinal fluid, bile, gastric juices, lymph, interstitial fluid, semen, synovial fluid, skin, mucous membrane tissue, hair, organ tissue, and combination thereof.

8. A method of preventing perfusion deficiency of an organ or part thereof in a human subject wherein the organ is the brain or part thereof, comprising administering a therapeutically effective amount of a compound of the general formula (4):

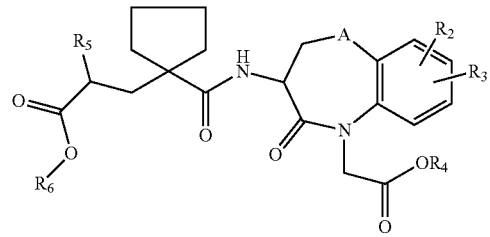

(4)

wherein A is CH$_2$,
wherein R2 and R3 independently represent hydrogen;
R4 and R6 independently represent hydrogen or a group that forms a biolabile carboxylic ester; and R5 is selected from the group consisting of -alkyl-(C1-C6)-phenyl, and -alkyl-(C1-C6)-naphthyl,
or a pharmaceutically acceptable salt or stereoisomer thereof; wherein the prevention of the perfusion deficiency is confirmed by measuring the presence or absence of an elevated concentration of a biomarker in one or more bodily fluids wherein the biomarker is selected from the group consisting of Endothelin-1 biomarker, pre-Endothelin-1, Pro-Endothelin (Big Endothelin-1), endothelin-1 converting enzyme (ECE-1), neutral endopeptidase (NEP), and human soluble endopeptidase (hSEP), and combinations thereof.

9. The method as recited in claim 8, wherein the pharmaceutically acceptable salt is selected from the group consisting of lithium salt, calcium salt, magnesium salt, and zinc salt.

10. The method as recited in claim 8, wherein the pharmaceutically acceptable salt is calcium salt.

11. The method as recited in claim 8, wherein the compound is administered parenterally to the subject at a dose of about 60 mg/kg per day.

12. The method as recited in claim 8, wherein the compound is administered subcutaneously.

13. The method as recited in claim 8, wherein the compound is administered as an implant.

14. The method as recited in claim 8, wherein the bodily fluid is selected from the group consisting of blood, blood plasma, saliva, tears, sweat, urine, cerebrospinal fluid, bile, gastric juices, lymph, interstitial fluid, semen, synovial fluid, skin, mucous membrane tissue, hair, organ tissue, and combination thereof.

15. The method as recited in claim 1, wherein the compound of formula (4) is (2R)-2-{[1-({[(3S)-1-(carboxymethyl)-2-oxo-2,3,4,5-tetrahydro-1H-1-benzazepin-3-yl]amino}carbonyl)cyclopent-yl]methyl}-4-phenylbutanoic acid having formula (6):

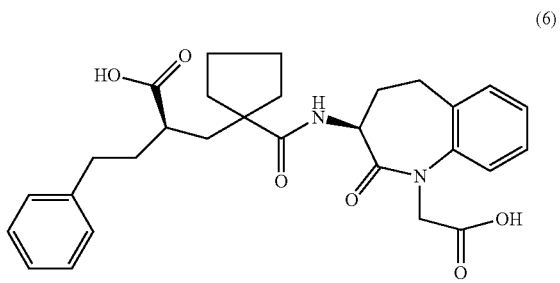 [SMILES: O=C(O)CN1C(=O)[C@@H](NC(=O)C2(C[C@@H](CCc3ccccc3)C(=O)O)CCCC2)CCc2ccccc21]

(6)

or a pharmaceutically acceptable salt thereof.

16. The method as recited in claim 1, wherein the compound of formula (4) is (2R)-2-{[{1-({[(3S)-1-(carboxymethyl)-2-oxo-2,3,4,5-tetrahydro-1H-1-benzazepin-3-yl]amino}carbonyl)cyclopent-yl]methyl}-4-(1-naphthyl)butanoic acid having formula (7):

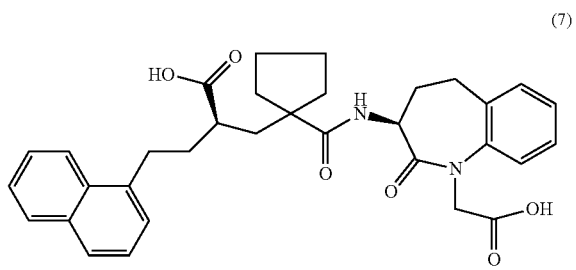 [SMILES: O=C(O)CN1C(=O)[C@@H](NC(=O)C2(C[C@@H](CCc3cccc4ccccc34)C(=O)O)CCCC2)CCc2ccccc21]

(7)

or a pharmaceutically acceptable salt thereof.

17. The method as recited in claim 1, wherein the compound is administered by oral administration.

18. The method as recited in claim 8, wherein the compound of formula (4) is (2R)-2-{[1-({[(3S)-1-(carboxymethyl)-2-oxo-2,3,4,5-tetrahydro-1H-1-benzazepin-3-yl]amino}carbonyl)cyclopent-yl]methyl}-4-phenylbutanoic acid having formula (6):

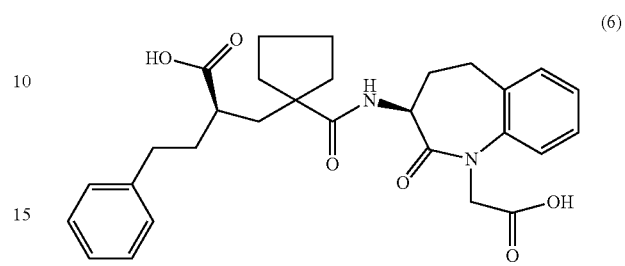

(6)

or a pharmaceutically acceptable salt thereof.

19. The method as recited in claim 8, wherein the compound of formula (4) is (2R)-2-{(1-({[(3S)-1-(carboxymethyl)-2-oxo-2,3,4,5-tetrahydro-1H-1-benzazepin-3-yl]amino}carbonyl)cyclopent-yl]methyl}-4-(1-naphthyl)butanoic acid having formula (7):

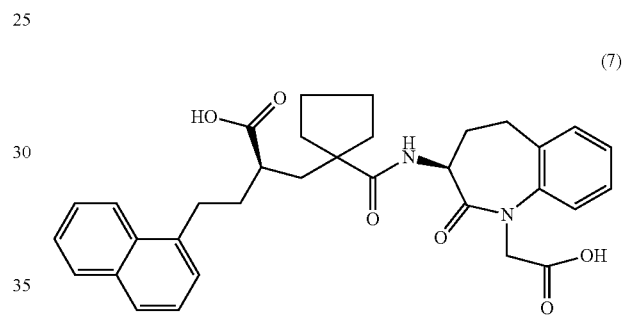

(7)

or a pharmaceutically acceptable salt thereof.

20. The method as recited in claim 8, wherein the compound is administered by oral administration.

* * * * *